United States Patent
Ferworn et al.

(10) Patent No.: US 7,249,009 B2
(45) Date of Patent: Jul. 24, 2007

(54) METHOD AND APPARATUS FOR SIMULATING PVT PARAMETERS

(75) Inventors: Kevin A. Ferworn, Houston, TX (US); John E. Zumberge, Houston, TX (US); John D. Ford, III, The Woodlands, TX (US)

(73) Assignee: Baker Geomark LLC, Houston, TX (US)

( * ) Notice: Subject to any disclaimer, the term of this patent is extended or adjusted under 35 U.S.C. 154(b) by 271 days.

(21) Appl. No.: 10/103,417

(22) Filed: Mar. 19, 2002

(65) Prior Publication Data

US 2003/0182061 A1  Sep. 25, 2003

(51) Int. Cl.
  G06G 7/48  (2006.01)
(52) U.S. Cl. .................................................... 703/10
(58) Field of Classification Search .................. 703/10; 702/6–16
  See application file for complete search history.

(56) References Cited

U.S. PATENT DOCUMENTS

| | | | |
|---|---|---|---|
| 4,893,505 A * | 1/1990 | Marsden et al. ......... | 73/152.24 |
| 5,337,822 A | 8/1994 | Massie et al. | |
| 5,778,154 A | 7/1998 | Bone et al. | |
| 6,106,561 A * | 8/2000 | Farmer ........................ | 703/10 |

FOREIGN PATENT DOCUMENTS

| | | |
|---|---|---|
| CA | 2185867 | 3/2000 |
| EP | 0 461 321 A1 | 12/1991 |
| WO | WO 99 57418 | 11/1999 |
| WO | WO 02 057596 * | 7/2002 |

OTHER PUBLICATIONS

John M. Hunt, Petroleum Geochemistry and Geology, 2nd. Edition, Published 1995, Publisher: W. H. Freeman & Co, ISBN: 0716724413, pp. 8, 419, 443, 444, 545, 548.*
Ridha B.C. Gharbi and Adel M. Elsharkawy, Neural Network Model for Estimating the PVT Properties of Middle East Crude Oils, SPE Reservoir Eval. & Eng., Jun. 1999.*
Kaufman et al., Characterizing the Greater Burgan Field Use of Geochemistry and Oil Fingerprinting, SPE 37803, Mar. 1997.*
Osman et al., Prediction of Oil PVT Properties Using Neural Networks, SPE 68233, Mar. 2001.*
Gharbi et al., Neural Network Model for Estimating PVT Properties of Middle East Crude Oils, SPE 56850, Jun. 1999.*
Birol Dindoruk and Peter G. Christman, PVT Properties and Viscosity Correlations for Gulf of Mexico Oils, SPE 71633, Oct. 2001.*

(Continued)

*Primary Examiner*—Paul L. Rodriguez
*Assistant Examiner*—Juan Carlos Ochoa
(74) *Attorney, Agent, or Firm*—Madan, Mossman & Sriram, P.C.

(57) ABSTRACT

A method and apparatus for converting downhole wireline logging measurements of pressure gradient, formation pressure and temperature into estimates of petroleum fluid PVT properties unaffected by oil-based drilling mud, without the need for retrieving actual petroleum samples from the borehole for laboratory analysis at the surface. The statistical accuracy of the PVT properties of reservoir fluids are enhanced with geochemical information of the fluids expected from a given reservoir.

12 Claims, 9 Drawing Sheets

OTHER PUBLICATIONS

Reservoir Geochemistry A Link Between Reservoir Geology and Engineering, SPE 28849, 1994.*

Westrich et al., Evaluating Reservoir Architecture in the Northern Gulf of Mexico With Oil and Gas Chemistry, SPE 59518, Dec. 1999.*

Kartoatmodjo and Schmidt, New Correlations For Crude Oil Physical Properties, SPE 23556, Jun. 1991.*

M.A. Mahmood, M.A. Al-Marhoun, Evaluation of Empirically Derived PVT Properties for Pakistani Crude Oils, Journal of Petroleum Science and Engineering, Jun. 12, 1996, pp. 275-290.

F. Gozalpour, A. Danesh, D.-H. Tehrani, A.C. Todd and B. Tohidi, Predicting Reservoir Fluid Phase and Volumetric Behaviour from Samples Contaminated with Oil-Based Mud, SPE International, 1999—SPE 56747, pp. 357-365.

V. Diatschenko, PVT—Comparison of Estimated to Measured Fluid Properties, Southwestern Petroleum Short Court—99, pp. 307-320.

A. Van Dusen, S. Williams, F. H. Fadnes, and J.Irvine-Fortescue, Determination of Hydrocarbon Properties by Optical Analysis During Wireline Fluid Sampling, Society of Petroleum Engineers (SPE 63252)—2000, pp. 773-785.

S.M. Hurst, T.F. McCoy, and M.P. Hows., Using the Cased-Hole Formation Tester Tool for Pressure Transient Analysis, Society of Petroleum Engineers (SPE 63078)—2000, pp. 449-463.

A.H. El-Banbi, and W.D. McCain, Jr., Sampling Volatile Oil Wells, Society of Petroleum Engineers (SPE 67232)—2001, pp. 1-6.

D. Ghorbani and R. Kharrat, Fluid Characterization of an Iranian Carbonate Oil Reservoir Using Different PVT Packages, Society of Petroleum Engineers (SPE 68745)—2001, pp. 1-7.

Iglesias-Silva et al., A Simple Equation Of State For Non-Polar Gases. Fluid Phase Equilibria, 67 (1991) pp. 87-98.

Avaullee et al., Thermodynamic Modeling For Petroleum Fluids II. Prediction Of PVT Properties Of Oils And Gases By Fitting One Or Two Parameters To The Saturation Pressures Of Reservoir Fluids. Fluid Phase Equilibria 139 (1997), pp. 171-203.

* cited by examiner

METHOD AND APPARATUS FOR SIMULATING PVT PARAMETERS

BACKGROUND OF THE INVENTION

1. Field of the Invention

This invention relates to a method for producing simulated PVT (Pressure-Volume-Temperature) parameters from well log information without the need to collect physical samples from petroleum reservoirs. In particular the invention relates to a computing apparatus which accepts wireline logging pressure and temperature measurements as a function of borehole depth and generates simulated PVT parameters. More particularly, the invention concerns enhancing the statistical accuracy of the PVT parameters with knowledge of geochemical characteristics of fluids of a reservoir of which the well is drilled.

2. Description of the Prior Art

Petroleum fluids (liquids and gas) are found in geological reservoirs where they are contained at high pressure (relative to ambient atmospheric pressure), and usually also at an elevated temperature (relevant to ambient atmospheric temperature). At such pressures, the reservoir fluid initially exists as a single-phase fluid, but will release dissolved gas to form a two-phase fluid with separate gas and oil components if the reservoir fluid has its initial pressure sufficiently reduced toward ambient atmospheric pressure. Also, the initial relatively high temperature of the reservoir fluid results in volumetric contraction of a given mass of fluid as it cools toward ambient atmospheric temperature if withdrawn from the well.

When petroleum exploration wells are drilled and hydrocarbon fluids are found, a well fluid test is usually performed. This test usually involves flowing the well fluid to the surface, mutually separating the oil and the gas in a separator, separately measuring the oil and gas flow rates, and then flaring the products.

It is also desirable to take samples of the oil and gas for chemical and physical analysis. Such samples of reservoir fluid are collected as early as possible in the life of a reservoir, and are analyzed in specialist laboratories. The information which this provides is vital in the planning and development of petroleum fields and for assessing their viability and monitoring their performance.

There are two ways of collecting these samples:
1. Open-hole Bottom Hole Sampling of the fluid directly from the reservoir, and
2. Surface Recombination Sampling of the fluid at the surface.

In Open-hole Bottom Hole Sampling (BHS) a special sampling tool is run into the well to obtain a pressurized sample of the formation fluid present in the well bore. During sampling, the pressure of the sample is maintained at the same downhole pressure at which it is obtained from the formation surrounding the borehole. Provided the well pressure at the sampling depth is above the "Saturation Pressure" of the reservoir fluid, the sample will be a single-phase fluid representative of the reservoir fluid, i.e. an aliquot.

Surface Recombination Sampling (SRS) involves collecting separate oil and gas samples from the surface production facility (e.g. from the gas/oil separator). These samples are recombined in the correct proportions at the analytical laboratory to create a composite fluid which is intended to be representative of the reservoir fluid, i.e. a re-formed aliquot.

Several Open-hole BHS tools are currently available commercially, which function by a common principle of operation. These include Schlumberger's MDT tool, Baker Atlas' RCI tool and Halliburton's RDT tool. As a group these are often referred to as Wireline Formation Test tools (WFT). A plurality of samples can be collected (e.g. from different producing zones) from one trip into the well.

A typical WFT tool is run into the well to tap a sample of reservoir fluid at the required depth by controlled opening of an internal chamber to admit reservoir fluid, followed by sealing of the sample-holding chamber after admission of predetermined volume of fluid. The tool is then retrieved from the well and the sample is transferred from the tool for shipment to the analytical laboratory. The downhole PVT characteristics of each sample is then determined.

Wireline Formation Test tools provide not only PVT quality samples at most promising intervals of the borehole, but also a pressure gradient and temperature profile log of the well. A pressure gradient is used to determine fluid contact level, formation fluid density and completion strategies. As mentioned above, the fluid samples collected by WFT tools are sent to analytical laboratories for PVT (pressure-volume-temperature) measurements.

Current well logging practice measures pressure profiles in multiple potential hydrocarbon producing zones and collects PVT quality samples in only the most promising intervals. The number of samples collected is limited because of:
1. The rig-time (cost) associated with running the wireline formation tester;
2. The time required to reduce the presence of oil-based drilling mud which contaminates samples and alters their PVT properties; and
3. The number of available chambers in the tool for sample collection.

In the past, there has been no convenient system or method by which the pressure profile and temperature profile measurements from the WFT log, for example, can be used to predict the PVT characteristics obtained from the samples obtained while obtaining the WFT log.

3. Identification of Objects of the Invention

A primary object of the invention is to provide a computer based analytical tool and method to produce PVT characteristics of petroleum reservoir fluids as a function of depth from pressure and temperature profile measurements from a logging tool without the need for collection of fluid samples.

Another object of the invention is to provide a computer based analytical tool and method to produce PVT characteristics of petroleum reservoir fluids as a function of depth from log measurements of formation pressure, temperature and pressure gradient derived from the formation pressure.

Another object of the invention is to provide PVT characteristics of reservoir fluids from logging tool measurements of reservoir pressure, reservoir temperature, and pressure gradient with information as to the physical location of the well which enables pertinent geochemical parameters to be identified for enhanced statistical accuracy of the PVT characteristics.

SUMMARY OF THE INVENTION

The objects identified above as well as other features and advantages of the invention are incorporated in a method for producing computer based modules which accept input data of formation pressure, temperature and pressure gradient, as a function of depth, and outputs data as a function of depth for any or all of several parameters such as reservoir fluid molecular weight (RF MW), Saturation Pressure ($P_{sat}$) and so on. A first module called PVT MOD includes equations which relate to output parameters as a function only of formation pressure, temperature and pressure gradient. A second module called PVT MOD PLUS includes equations which relate the output parameters not only as a function of formation pressure, temperature and pressure gradient, but also the geochemical parameters representing source rock type (aromaticity), thermal maturity and biodegradation. Such geochemical parameters are determined by inputting information as to the physical location of the well into a database which relates geochemical parameters to well locations. Thus, when using PVT MOD PLUS, six parameters, as a function of depth are input to the module and any or all of the several parameters mentioned above are output as a function of depth. The statistical accuracy of the estimation of the PVT output variables from the PVT MOD PLUS module is enhanced over that obtained from the PVT MOD module.

DESCRIPTION OF THE INVENTION

This invention relates to providing computer based models which produce outputs of estimates of petroleum fluid properties of petroleum reservoir fluids (called PVT parameters or characteristics) without the need for laboratory analysis of fluid samples and phase behavior as a function of input data. For a first module, called PVT MOD, the input parameters are three data, each determined as a function of depth in a borehole from a wireline logging tool such as a wireline formation tester. For a second module called PVT MOD PLUS, improved output estimates of PVT parameters are obtained by adding one or more geochemical parameters to the equations of the model, and the method includes the input parameters of the PVT MOD plus the location of the well which through a database provides the geochemical parameters of the equation. Preferably, three geochemical parameters are employed with the PVT MOD PLUS: source rock type (aromaticity), thermal maturity and biodegradation.

The three preferred parameters determined from a Wireline Formation Test tool are reservoir fluid density, reservoir pressure and reservoir temperature. Reservoir fluid density is determined from a measurement of downhole pressure gradient:

$$\rho_f = \frac{\Delta p / \Delta z}{g}, \quad (1)$$

where $\Delta p/\Delta z$ is the pressure gradient (z is depth), $\rho_f$ is the reservoir fluid density and g is the gravitational constant. When reservoir fluid density is determined from equation (1), it is not affected by the presence of oil-based drilling mud, the presence of which contaminates actual PVT samples leading to errors in laboratory measured PVT parameters. With independent knowledge of the oil based drilling mud density, the reservoir fluid density can also be determined from information of the mud hydrostatic pressure gradient:

$$\rho_f = \rho_m(\Delta p_f/\Delta p_m) \quad (2)$$

where, $\rho_f$=mud free reservoir fluid density,
$\rho_m$=oil-based drilling mud density,
$\Delta P_f$=formation pressure gradient,
$\Delta P_m$=hydrostatic pressure gradient.

The computer modules PVT MOD and PVT MOD PLUS are based on the reservoir fluid density $\rho_f$ (from equation (1)) or $\rho_f$ (from equation (2)). As described below while referring to FIG. 1, a set of 145 reservoir fluid PVT reports from the Gulf of Mexico representing a wide range of petroleum fluid types was used to produce the PVT MOD equations. The PVT MOD PLUS discussed by reference to FIG. 2, uses, in addition, geochemical parameters as a function of 3,700 global oil well locations. Samples of each of the 3,700 wells are each associated with three fundamental geochemical parameters:

SRA=Source Rock Aromaticity
TM=Thermal Maturity
BIO=Biodegradation

The equations of PVT MOD PLUS enhance the statistical accuracy of the PVT MOD equation.

Figure 1:
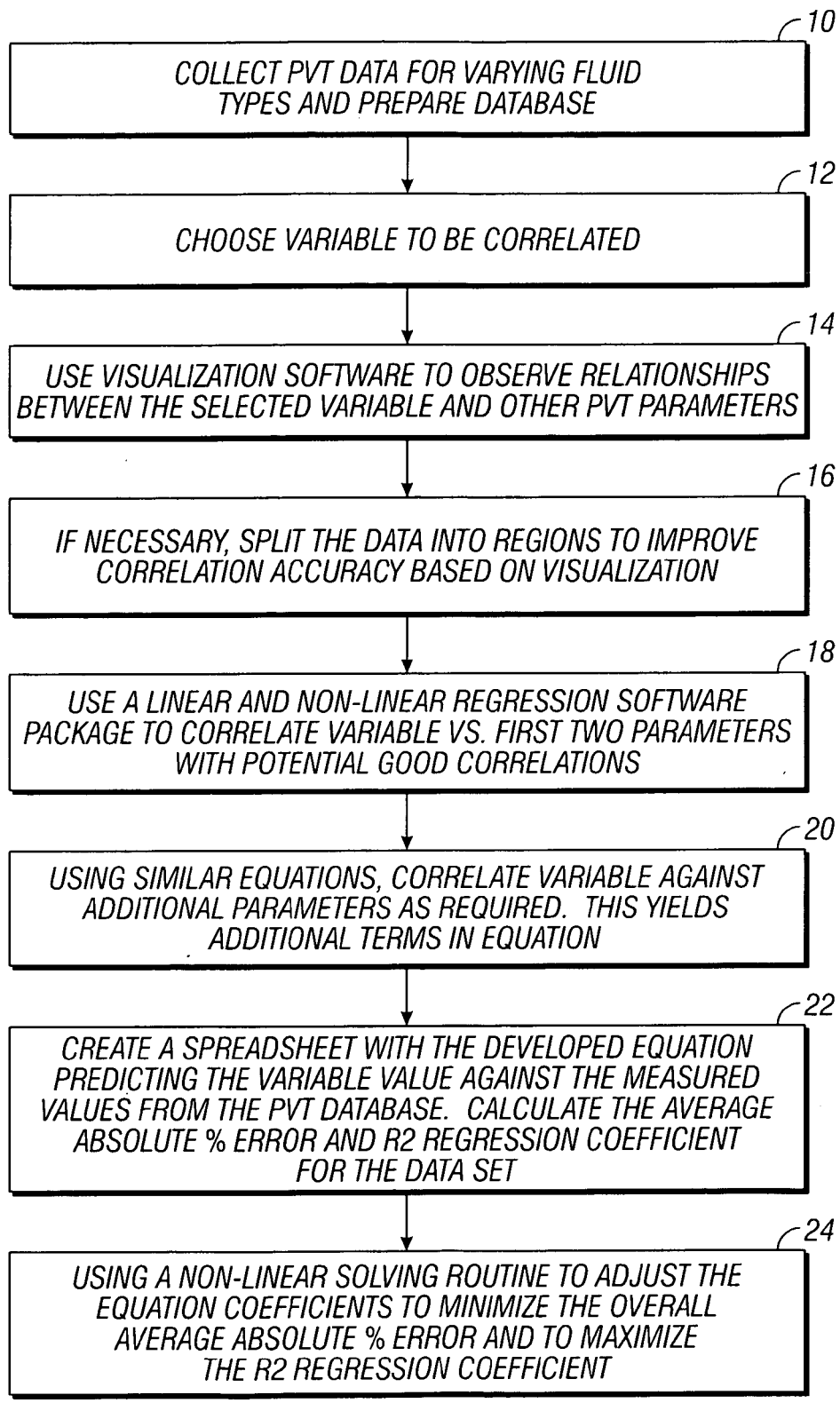
FIG. 1 is a flow chart of the steps used to generate modules of equations (called PVT MOD equations) which relate any or all parameters such as reservoir fluid viscosity to input parameters of formation pressure, temperature, and pressure gradient.

FIG. 1 is a flow chart which illustrates the method used to develop the PVT MOD module equations for predicting PVT parameters. First, as indicated by logic box 10 a Ski)

database of PVT measurements is constructed, ideally representing a wide range of fluid types from dry gas condensates to heavy black oils. With the database in place, each significant PVT parameter is correlated by following a standard procedure as described below.

A variable to be correlated is chosen, as in Logic Box 12, that is a variable of interest and is "visualized" with Visualization software (as in logic box 14) as a function of the other parameters available in the PVT database. For example, if the variable is plotted on Cartesian coordinates against a single parameter, the importance of additional parameters can be observed by adjusting the size, shape, color, orientation, etc. of the data points in accordance with the additional parameters. The result is an estimation of which parameters are related to the variable under consideration. During the visualization process, it is useful, as indicated by Logic Box 16, to separate the variable into multiple groups to tighten the correlations.

After the likely parameters have been selected, a linear/non-linear, three-dimensional regression software package is used as indicated in Logic Box 18 to select a specific correlation of the variable against the first two parameters from the visualization. The resulting equation is further enhanced by alternating the additional parameters and completing new regressions, as indicated by Logic Box 20. The final result of this step is an equation with multiple terms (parameters and coefficients) that correlate with the variable of interest.

With the new equation from Logic Box 20, a spreadsheet is prepared as indicated by Logic Box 22 with the PVT data to calculate the variable of interest. In addition to the average errors calculated for each data point, an overall average absolute percent error and least squares regression coefficient are calculated for the complete data set. To improve the final accuracy of the equation, a linear/non-linear solving routine (such as Excel's Solver™), as indicated by Logic Box 24, is used to adjust the coefficients thereby reaching a minimum average absolute percent error and a maximum regression coefficient.

Each of the other parameters is calculated following the same procedure. The result is a group of equations (called PVT MOD equations) that relate each output variable or parameter of interest as a function of input formation pressure, temperature and pressure gradient (from which reservoir fluid density $\rho_f$ can be calculated).

Figure 2:
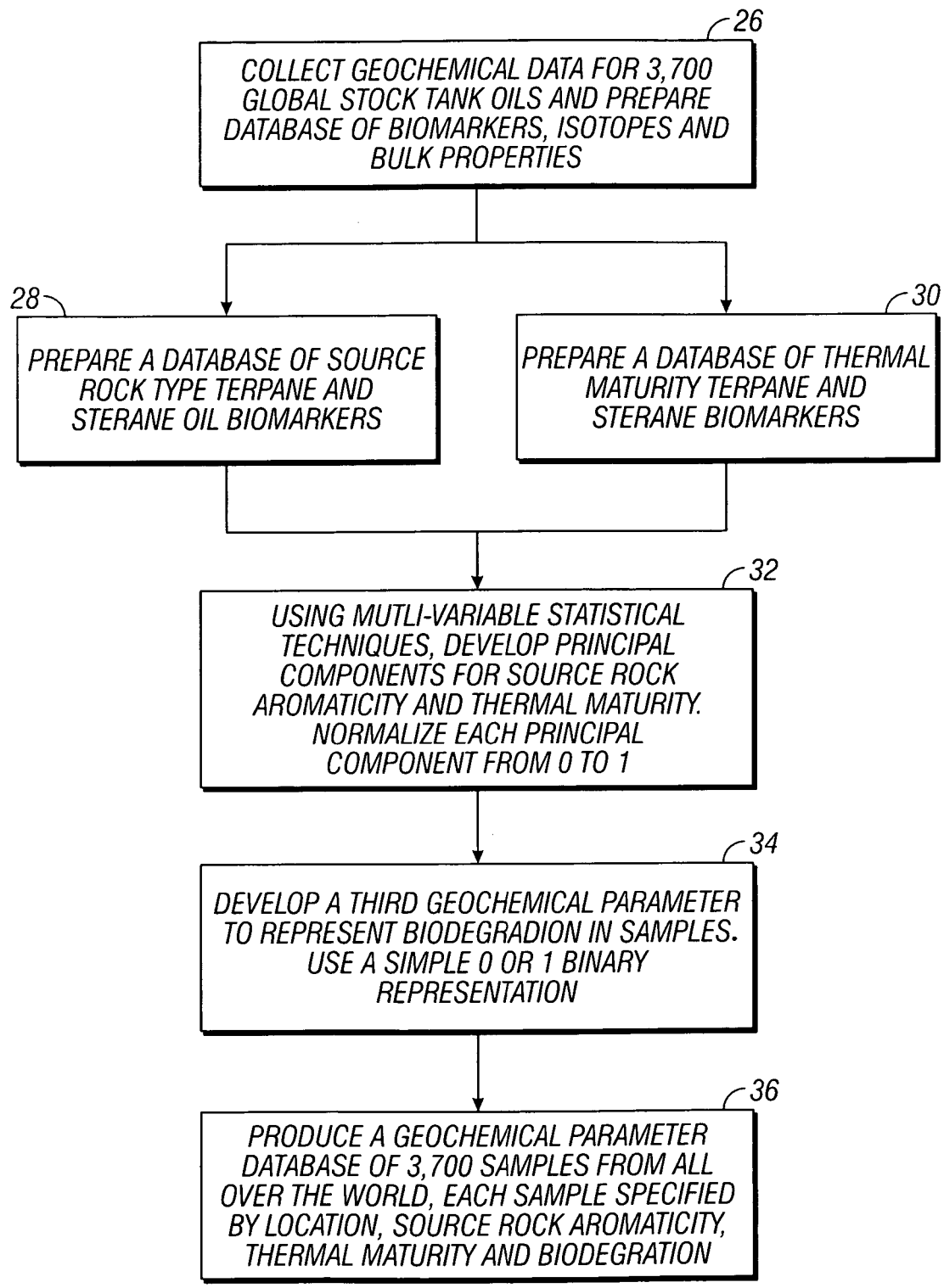
FIG. 2 is a flow chart of the steps taken to develop a global database of stock tank oils to determine parameters of Source Rock Aromaticity, Thermal Maturity and Biodegradation as a function of the location of the well.

FIG. 2 is a flow chart which illustrates the method according to the invention to develop geochemical parameters that improve the predictive accuracy of the PVT MOD equations. Three geochemical parameters preferred in this invention representing source rock type (aromaticity), thermal maturity and biodegradation are developed in the current invention. One, two or all three of the geochemical parameters may be used.

A database of 3,700 global stock tank oil geochemical analyses, including sterane and terpane biomarkers, stable carbon isotopes and bulk properties, were collected as indicated by Logic Box 26. From this data, sub-databases of specific source rock (Logic Box 28) and thermal maturity parameters (30) are prepared based on the geologic framework of each basin where the oils were obtained. The parameters most indicative of source rock aromaticity are tricyclic terpane ratios such as C19/C23, C24/C23, C26/C25 and pentacyclic terpanes such as C31/C30 and C29/C30. The parameters relating to thermal maturity include the relative quantities of diasteranes and diahopanes to regular steranes and hopanes as well as trisnorhopane ratios. For each dataset, a multi-variable statistical technique is used as indicated in Logic Box 32 to create a "principal component," which is a linear combination of each of the included parameters. For both the source rock aromaticity and the thermal maturity, the principal components are normalized from 0 to 1.

A third geochemical parameter is developed as in Logic Box 34 to represent biodegradation of the samples. This parameter is less predictive than the source rock aromaticity or thermal maturity and therefore, a 0 or 1 binary representation is used.

These three geochemical parameters are included in a database which further contains the PVT parameters used to develop the equation of PVT MOD PLUS per the method outlined in FIG. 1. The three geochemical data parameters are included in the PVT data sample of Logic Box 36 of FIG. 2.

To illustrate the development of the equations using the six variables as described above, a first equation for the output variable reservoir fluid methane content is demonstrated. FIGS. 3 through 6 are presented to illustrate the method.

Figure 3:
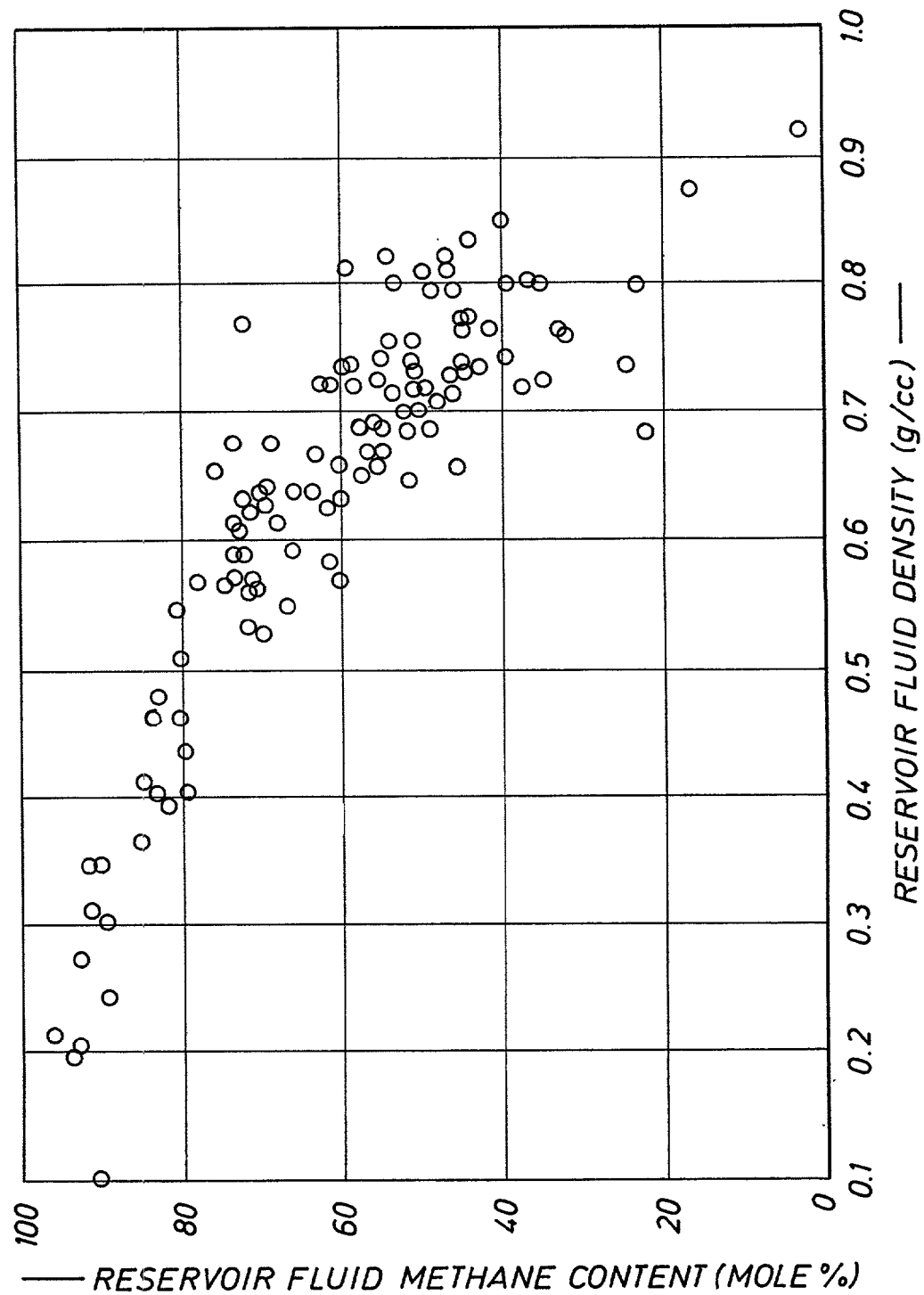
FIG. 3 is a graph of reservoir fluid methane content as a function of reservoir fluid density illustrating a step in the method of generating the equations of FIG. 1.

FIG. 3 is a graph of Reservoir Fluid Methane content (mole %) versus Reservoir Oil Density (g/cc) from the 145 laboratory PVT reports in the Gulf of Mexico. From FIG. 3, it is apparent that a general relationship exists between reservoir fluid methane content and density and that that relationship is particularly strong at high methane content values. However, further consideration of the available data is worthwhile to determine if additional parameters would improve the correlation.

Figure 4:
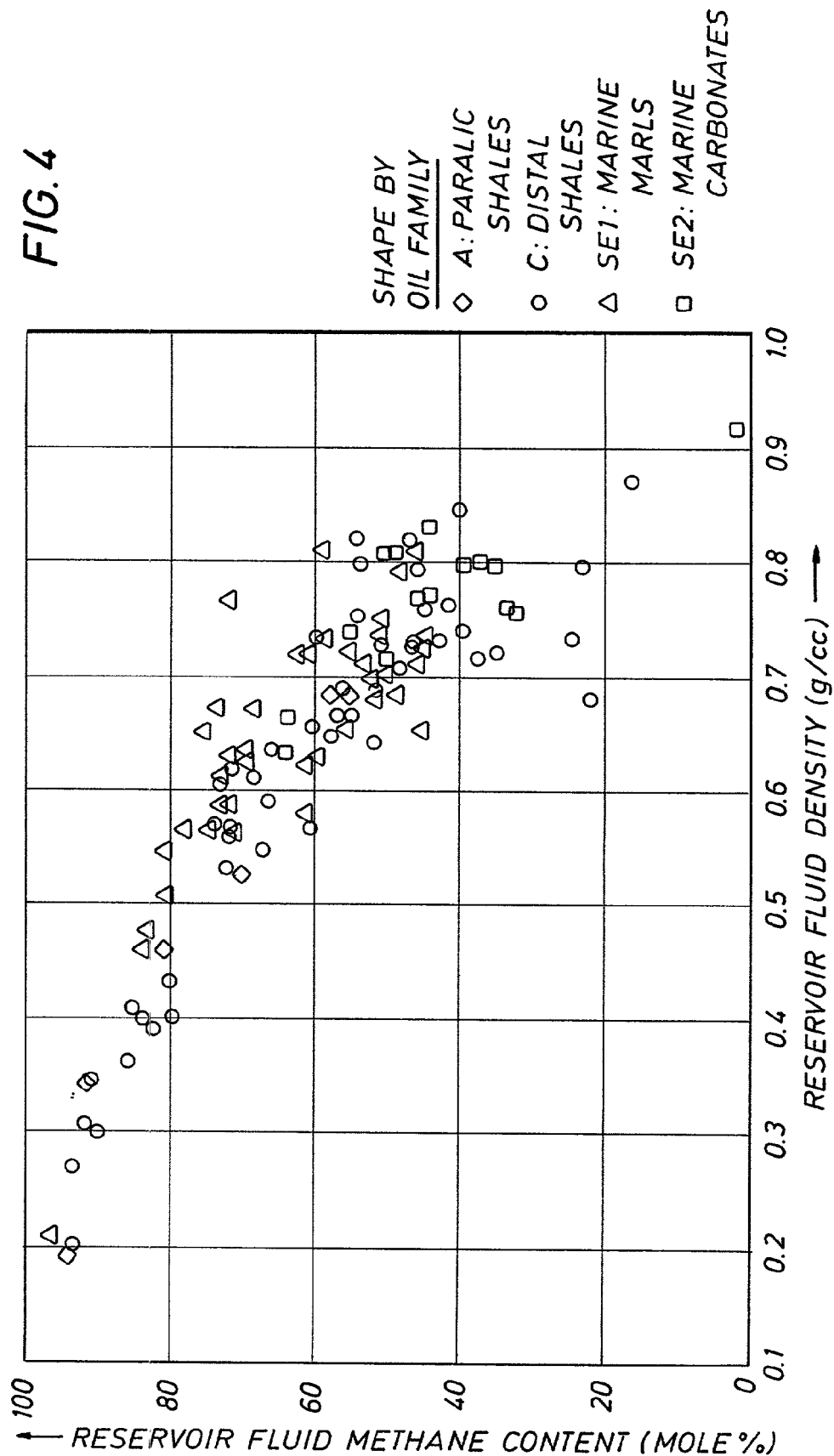
FIG. 4 is a graph of the same parameters as of FIG. 3, but the data points or "samples" have been coded by their source rock type.

FIG. 4 presents the same data and scales from FIG. 3 but in this graph, the data point symbols have been coded by their Source Rock type. As an example, note the SE1 family samples (from Marine Marl source rocks) appear to group on the upper section of the curve.

From this observation, it appears that Source Rock type does have an influence on the relationship between reservoir fluid methane content and density; however, further consideration is warranted to determine why some marine marl symbols cluster in different regions than others.

Figure 5:
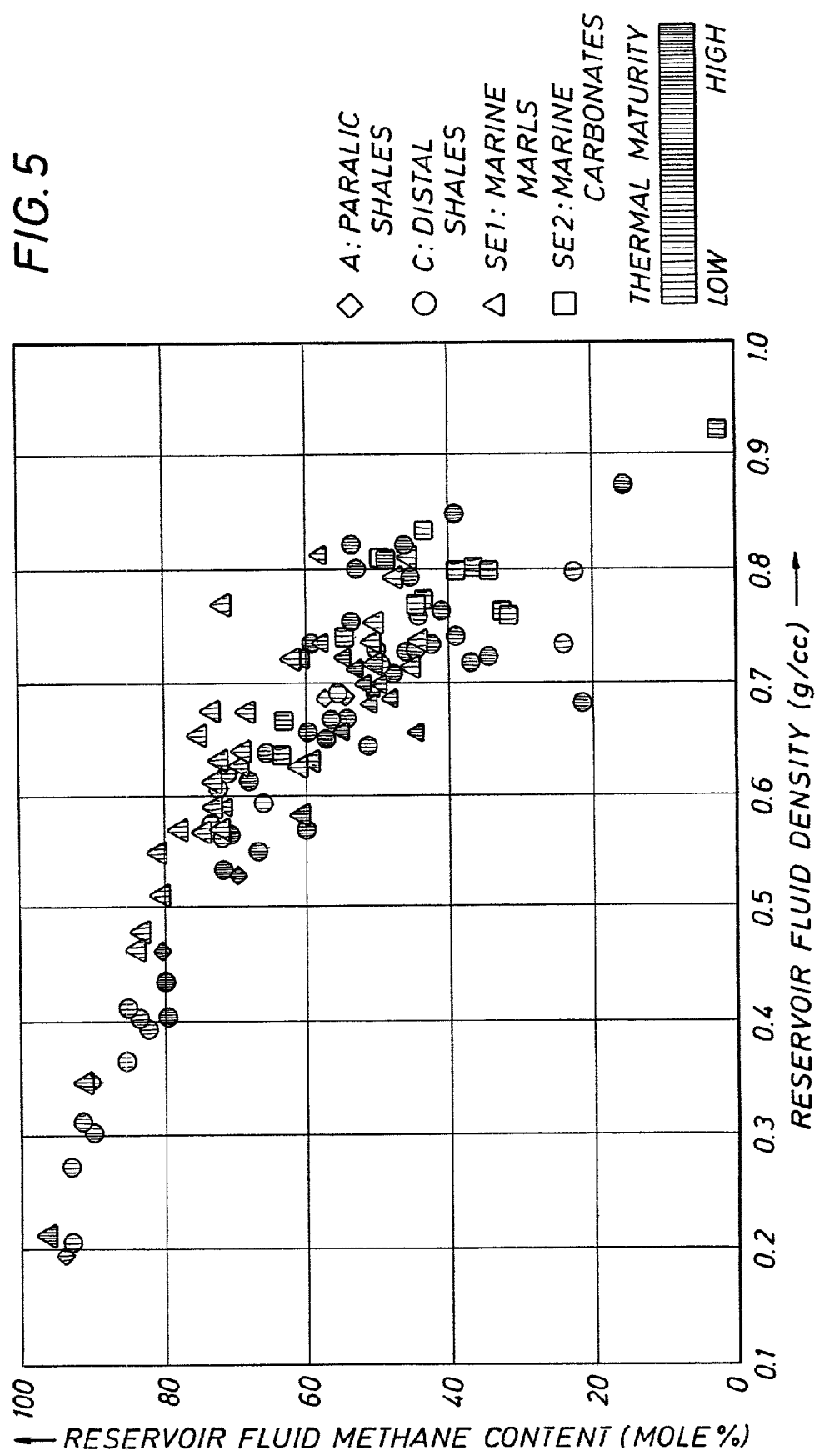
FIG. 5 is a repeat of FIG. 4 except that the shading of the symbols indicates their thermal maturity and shows that more mature samples (those with darkest shading) cluster together near the lower end of the curve indicating that thermal material is a useful parameter in discovering an equation that relates reservoir fluid methane content as a function of reservoir fluid density.

FIG. 5 is a repeat of FIG. 4 except the shade of the symbols has been made a function of their Thermal Maturity. From FIG. 5, it is clear that more mature samples (those with the darkest symbols) cluster together near the lower end of the general curve. From this observation it appears that Thermal Maturity is a useful parameter when predicting reservoir fluid methane content from reservoir fluid density.

Figure 6:
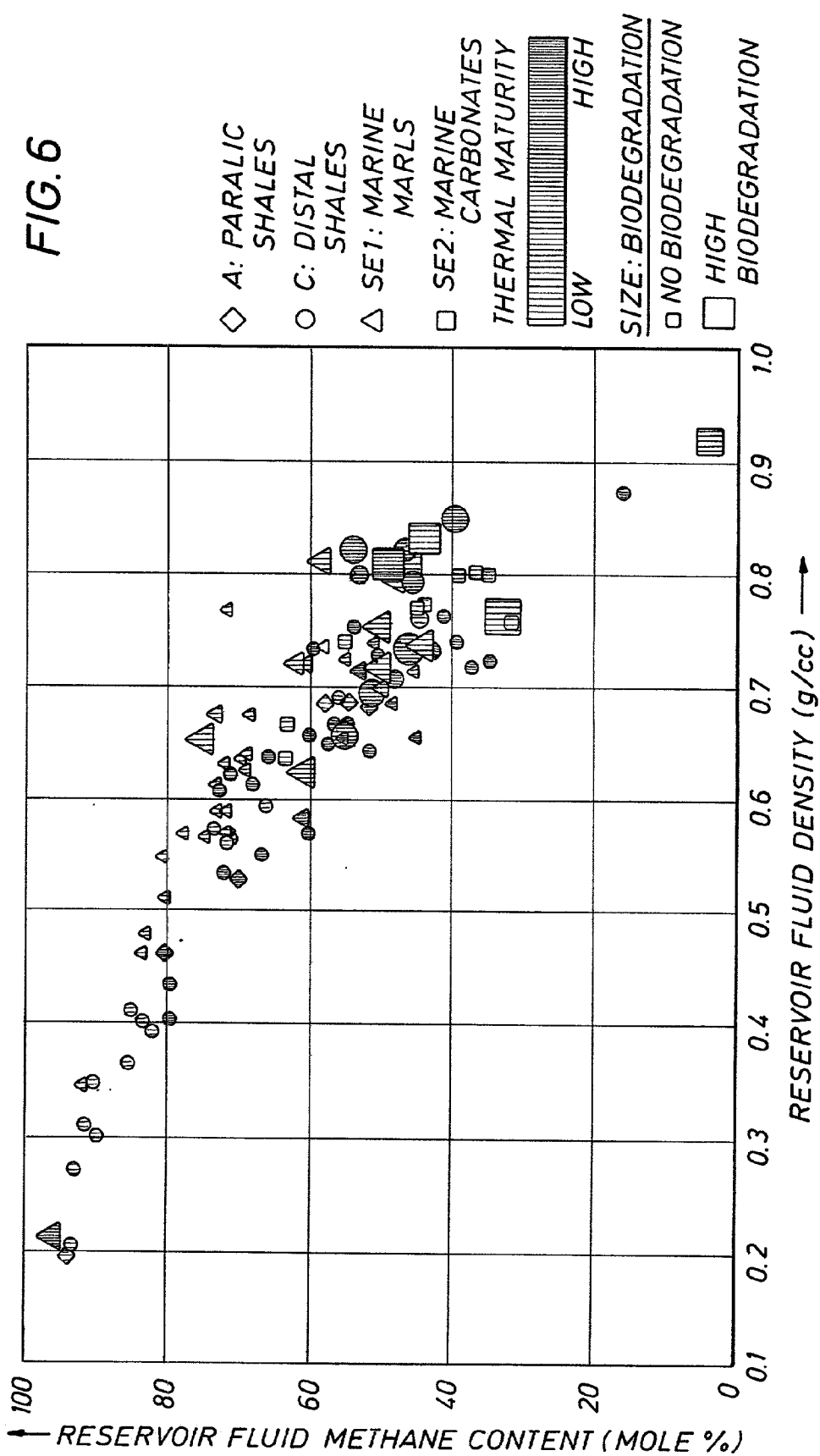
FIG. 6 is another graph of reservoir fluid methane content as a function of reservoir oil directly with biodegraded samples clustered near the lower right hand of the graph indicating the additional improvement in the correlation can be made by including biodegradation in the equation relating reservoir fluid methane content and reservoir oil density.

FIG. 6 is a final graph of reservoir fluid methane content versus density data where the largest symbols now represent biodegraded samples. From this figure it can be seen that the biodegraded samples cluster near the lower right section of the data set; this suggests a small improvement in the correlation can be made by the inclusion of a biodegradation term in the final equation.

From the above, a set of equations using the method of FIG. 1 can be defined which relate output variables to input measured variables of $\rho_f$, $P_{res}$ and $T_{res}$ to obtain a PVT MOD module set of equations. Table 1 below shows the input variable and output variable functionality for each equation for the PVT MOD system. Notice that each output variable can be determined from one of the input variables or as a function of one or more input variables and one or more of the previously determined output PVT variables.

TABLE 1

| OUTPUT PVT VARIABLE | INPUT VARIABLE(S) |
|---|---|
| Reservoir Fluid Viscosity ($\mu$) | $\rho_f$ |
| Reservoir Fluid Methane Content ($C_1$) | $\rho_f$, $P_{res}$, $T_{res}$ |
| Reservoir Fluid Heptane+ Content ($C_{7+}$) | $\rho_f$ |
| Reservoir Fluid Molecular Weight (RFMW) | $\rho_f$, $P_{res}$, $T_{res}$ |
| Single-Stage Gas Oil Ratio (GOR) | RFMW, $T_{res}$ |
| Stock Tank Oil Sulfur Content (% S) | RFMW |
| Reservoir Fluid Nitrogen Content ($N_2$) | RFMW |
| Saturated Formation Volume Factor (FVF) | RFMW, $T_{res}$ |
| Reservoir Fluid Heptane+ MW ($C_{7+}$ MW) | % S |
| Reservoir Fluid Heptane+ SG ($C_{7+}$ SG) | % S |
| Saturation Pressure ($P_{sat}$) | $C_1$, $C_{7+}$MW, $T_{res}$ |
| Stock Tank Oil API Gravity (API) | $C_{7+}$SG |
| Reservoir Fluid Ethane Content ($C_2$) | $C_1$, $C_{7+}$ |
| Reservoir Fluid Propane Content ($C_3$) | $C_1$, $C_{7+}$ |
| Reservoir Fluid n-Butane Content ($nC_4$) | $C_1$, $C_{7+}$ |
| Reservoir Fluid i-Butane Content ($iC_4$) | $nC_4$ |
| Reservoir Fluid n-Pentane Content ($nC_5$) | $C_1$, $C_{7+}$ |
| Reservoir Fluid i-Pentane Content ($iC_5$) | $nC_5$ |
| Reservoir Fluid Hexane Content ($C_6$) | $C_1$, $C_{7+}$ |
| Flash Gas Gravity (Gas Gravity) | $C_1$, $C_2$, $C_3$, $iC_4$, $nC_4$ |
| Flash Gas Gross Heating Value (BTU/scf) | Flash Gas Gravity |

Table 2 below shows each output PVT variable as a function of not only the input parameters of pressure-gradient (converted to $\rho_f$), $P_{res}$ and $T_{res}$, but also geochemical parameters of Source Rock Type (SRA), Thermal Maturity (TM) and Biodegradation (BIO).

TABLE 2

| OUTPUT PVT VARIABLE | INPUT VARIABLE(S) |
|---|---|
| Reservoir Fluid Viscosity ($\mu$) | $\rho_f$ |
| Reservoir Fluid Methane Content ($C_1$) | $\rho_f$, $P_{res}$, $T_{res}$, SRA, TM, BIO |
| Reservoir Fluid Heptane+ Content ($C_{7+}$) | $\rho_f$, SRA, TM |
| Reservoir Fluid Molecular MW (RFMW) | $\rho_f$, SRA, TM, $P_{res}$, $T_{res}$ |
| Single-Stage Gas Oil Ratio (GOR) | RFMW, BIO |
| Stock Tank Oil Sulfur Content (% S) | RFMW, SRA, BIO |
| Saturated Formation Volume Factor (FVF) | RFMW, $T_{res}$ |
| Reservoir Fluid Nitrogen Content ($N_2$) | RFMW, SRA |
| Reservoir Fluid Heptane+ MW ($C_{7+}$MW) | % S, SRA |
| Reservoir Fluid Heptane+ SG ($C_{7+}$SG) | % S, SRA |
| Saturation Pressure ($P_{sat}$) | $C_1$, SRA, TM, $C_{7+}$MW, $T_{res}$ |
| Stock Tank Oil API Gravity (API) | $C_{7+}$SG, SRA |
| Reservoir Fluid Ethane Content ($C_2$) | $C_1$, $C_{7+}$ |
| Reservoir Fluid Propane Content ($C_3$) | $C_1$, $C_{7+}$ |
| Reservoir Fluid i-Butane Content ($iC_4$) | $NC_4$, SRA |
| Reservoir Fluid n-Butane Content ($nC_4$) | $C_1$, $C_{7+}$ |
| Reservoir Fluid i-Pentane Content ($iC_5$) | $NC_5$, SRA |
| Reservoir Fluid n-Pentane Content ($nC_5$) | $C_1$, $C_{7+}$ |
| Reservoir Fluid Hexane Content ($C_6$) | $C_1$, $C7_+$ |
| Flash Gas Gravity (Gas Gravity) | $C_1$, $C_2$, $C_3$, $iC_4$, $nC_4$, SRA |
| Flash Gas Gross Heating Value (BTU/scf) | Gas Gravity |

The equation functional relationships indicated in Table 2 are developed from the relationships first developed in Table 1. The variables of reservoir pressure ($P_{res}$), temperature ($T_{res}$) and density ($\rho_f$) were used to develop the relationship of Table 1 from individual PVT reports collected for a wide range of fluid types from the Gulf of Mexico reservoirs. As indicated above, FIGS. 3 through 6 indicate visually that reservoir fluid methane ($C_1$) is a function not only of reservoir fluid density ($\rho_f$), but also rock aromaticity (SRA), thermal maturity (TM), and Biodegradation (BIO).

To develop the equation relationship between C1 and $\rho_f$, $P_{res}$, $T_{res}$, SRA, TM and BIO (for example), all the data for $C_1$, $\rho_f$, and SRA are loaded into a software package for multi-component regression called JANDEL Scientific Table Curve 3D™. Two equations are generated using that program (one for light samples where reservoir fluid molecular weight <50 g/mole and a second for heavy samples with RFMW>50 g/mole) where $C_1$ is a function of two primary variables: $\rho_f$ and SRA. Next, the reservoir fluid methane content $C_1$ and density $\rho_f$ values are applied again to the Table Curve software package, this time with thermal maturity (TM) parameters. The resulting model yields equations with a term representing thermal maturity (TM). The process is repeated a second time to produce terms appropriate for the influence of biodegradation (BIO). Similar methods are used to develop terms for the reservoir pressure ($P_{res}$) and reservoir temperature ($T_{res}$).

Adding the terms together, a general format of the two equations to calculate reservoir fluid methane content $C_1$ as a function of $\rho_f$, $P_{res}$, $T_{res}$, SRA, TM and BIO is developed of the form, $$C_{1\ RFMW<50\ g/mole} = k_1 + k_2\rho_f^{0.5} \ln(\rho_f) + k_3 P_{res}^2 \ln(P_{res}) + k_4 T_{res}^{1.5} \quad (3)$$

$$C_{1\ RFMW\geq 50 g/mole} = k_5 + k_6\rho_f^{0.5}\ln(\rho_f) + k_7 P_{res}^2 \ln(P_{res}) + k_8 T_{res}^{1.5} + k_9 \frac{\ln(SRA)}{(SRA)^2} + k_{10} TM^{k_{92}} + k_{11}(BIO) \quad (4)$$

where $C_1$=reservoir fluid methane content
$\rho_f$=reservoir fluid density
$P_{res}$=reservoir pressure
$T_{res}$=reservoir temperature
SRA=source rock aromaticity
TM=thermal maturity
BIO=biodegradation
$k_1 \ldots k_{11}$=constants Next, equations (3) and (4) are programmed in the software spreadsheet program Microsoft Excel™ allowing for the calculation of reservoir fluid methane contents $C_1$ for each point in the data set assuming an initial set of constants, $k_1$ through $k_{11}$. With those values calculated, the overall average absolute percent error is determined by averaging the individual errors for each point. Additionally, the $R^2$ regression coefficient for the data set is determined using the equation, $$R^2 = \frac{1 - \sum (C_1^{meas.} - C_1^{calc.})_1^2}{\sum (C_1^{meas.} - C_1^{ave.})_1^2} \quad (5)$$

Next, the Excel Solver routine is used to adjust the constants $k_1 \ldots k_{11}$ to achieve the best fit of the experimental data until the calculated average absolute percent error is minimized and the $R^2$ regression coefficient of equation (5) is maximized.

The above method is applied to obtain the equation for PVT MOD according to the functional relationship as indicated in Table 1. The input variables $\rho_f$, $P_{res}$, $T_{res}$ and the output PVT variables are obtained solely from relationships of 145 samples from the Gulf of Mexico reservoirs of stock tank oil geochemistry parameters and reservoir fluid PVT data.

For the PVT MOD PLUS equations, source rock aromaticity, thermal maturity and biodegradation indicators were added to each of the 145 samples and equations developed according to the functional relationships as indicated in Table 2.

Appendix I to this specification specifies each equation, like the equation (3) developed above for both PVT MOD (Table 1) and PVT MOD PLUS (Table 2) relationships. The numerical values of each of the constants can be determined by collecting a statistically significant sample set from a given region, e.g., the Gulf of Mexico reservoirs and determining the constants as described above by reference to equation (5). The database of geochemical parameters as a function of location can be derived from a database called GeoMark OILS™ available commercially from GeoMark Research, Inc. of Houston, Tex.

Figure 7:
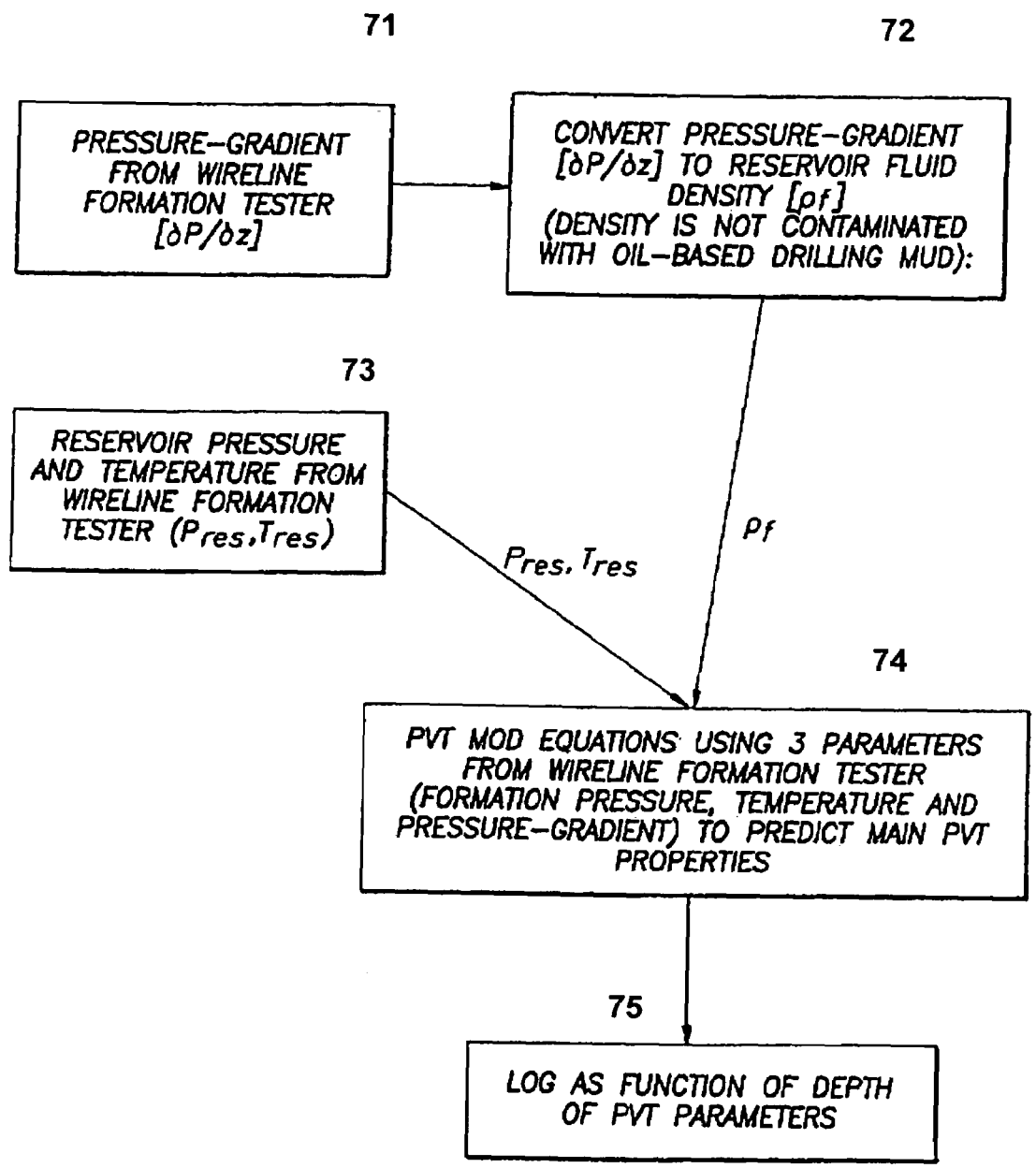
FIG. 7 is a flow chart of the method according to the invention to determine PVT parameters of petroleum fluids in formations surrounding a borehole by using information from a logging tool such as a Wireline Formation Tester with PVT MOD equation developed from sample data.

FIG. 7 outlines the method of the invention for generating simulated PVT parameters from well log data as a function of depth from pressure gradient; reservoir pressure and reservoir temperature. A shown in Logic Box 71, pressure-gradient [∂P/∂Z] is obtained from a wireline formation tester well log data, for example from Logic Box 110 of FIG. 9. Pressure-gradient is converted to reservoir fluid density $\rho_f$, as shown in Logic Box 72. This fluid density is not contaminated with oil-based drilling mud. Reservoir pressure $P_{res}$ and reservoir temperature $T_{res}$, see Logic Box 73, are obtained from wireline formation tester well log data. The reservoir pressure, reservoir temperature, and fluid density are input to PVT MOD equations in Logic Box 74, to predict main PVT parameters, as indicated above. The PVT MOD equations described above produce a log of the previously identified PVT parameters as a function of depth, as shown in Logic Box 75.

Figure 8:
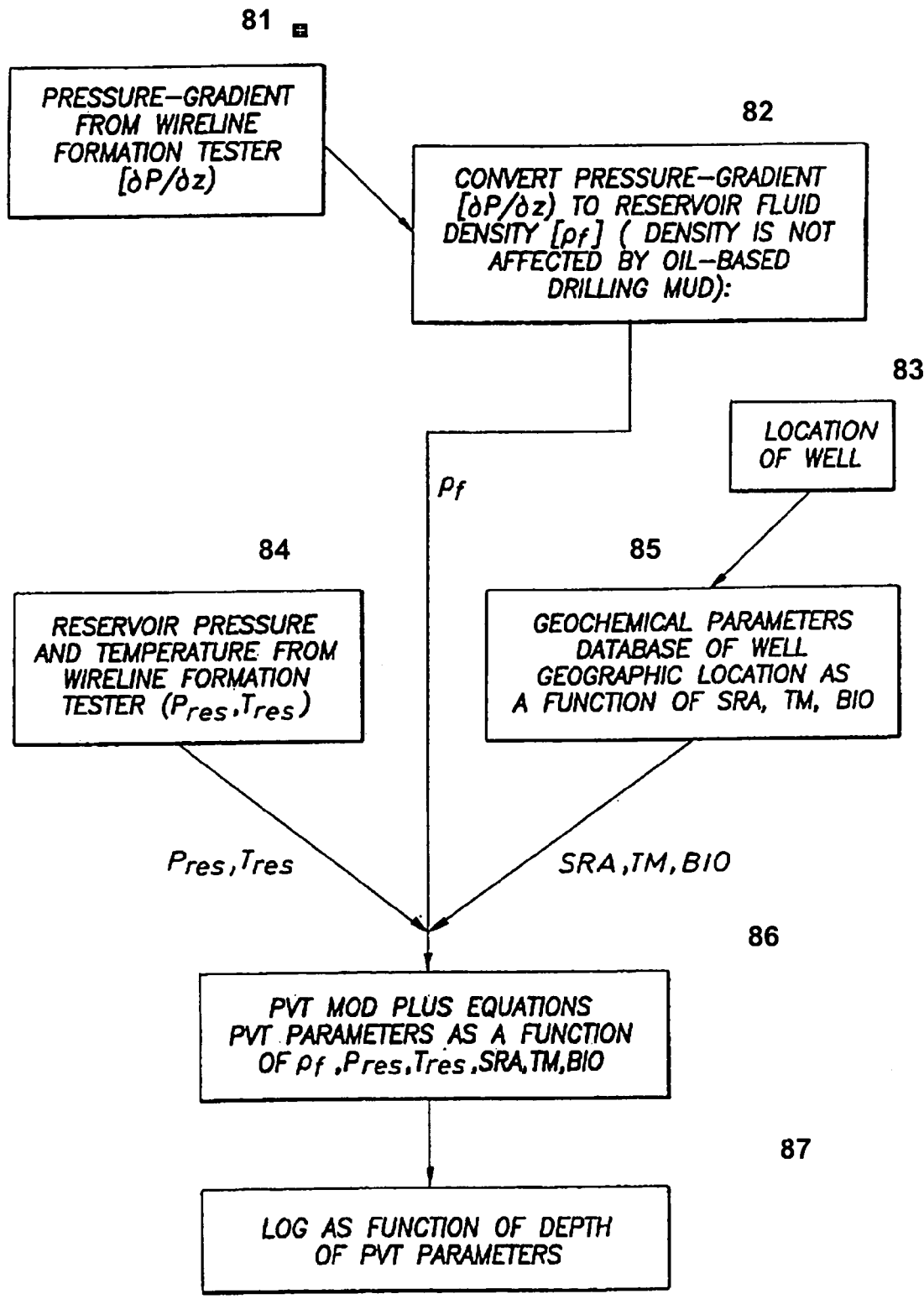
FIG. 8 is a flow chart of the method according to the invention to determine PVT parameters of petroleum fluids in formations surrounding a borehole using not only the input parameters of FIG. 7, but also geochemical parameters obtained from a global database of stock tank oils with location and geochemical parameter data as described in FIG. 2 with PVT MOD PLUS equations developed from sample data with geochemical data added thereto.

FIG. 8 outlines a method of the invention for creating a log of PVT Parameters from well log data like that of FIG. 7, but additionally includes well location information. In Logic Box 81, pressure-gradient [∂P/∂Z] is obtained from a wireline formation tester well log data, for example from Logic Box 110 of FIG. 9. Pressure-gradient is converted to reservoir fluid density $\rho_f$ in Logic Box 82. As discussed above, this fluid density is not contaminated with oil-based drilling mud. Reservoir pressure $P_{res}$ and reservoir temperature $T_{res}$, see Logic Box 84, also are obtained from wireline formation tester well log data . Well location is determined as shown in Logic Box 83. Well location is then used to determine SRA, TM, and BIO parameters from a database of Geochemical Parameter as a function of location, see Logic Box 85. The reservoir pressure, reservoir temperature, and fluid density are input, along with the Geochemical Parameters (SRA, TM, and BIO) to PVT MOD PLUS equations, as shown in Logic Box 86, to predict the previously described PVT parameters as a function of the input parameters, $\rho_f$, $T_{res}$, $P_{res}$, SRA, TM, and BIO. The PVT MOD PLUS equations described above produce a log of the previously identified PVT parameters as a function of depth, as shown in Logic Box 87.

Figure 9:
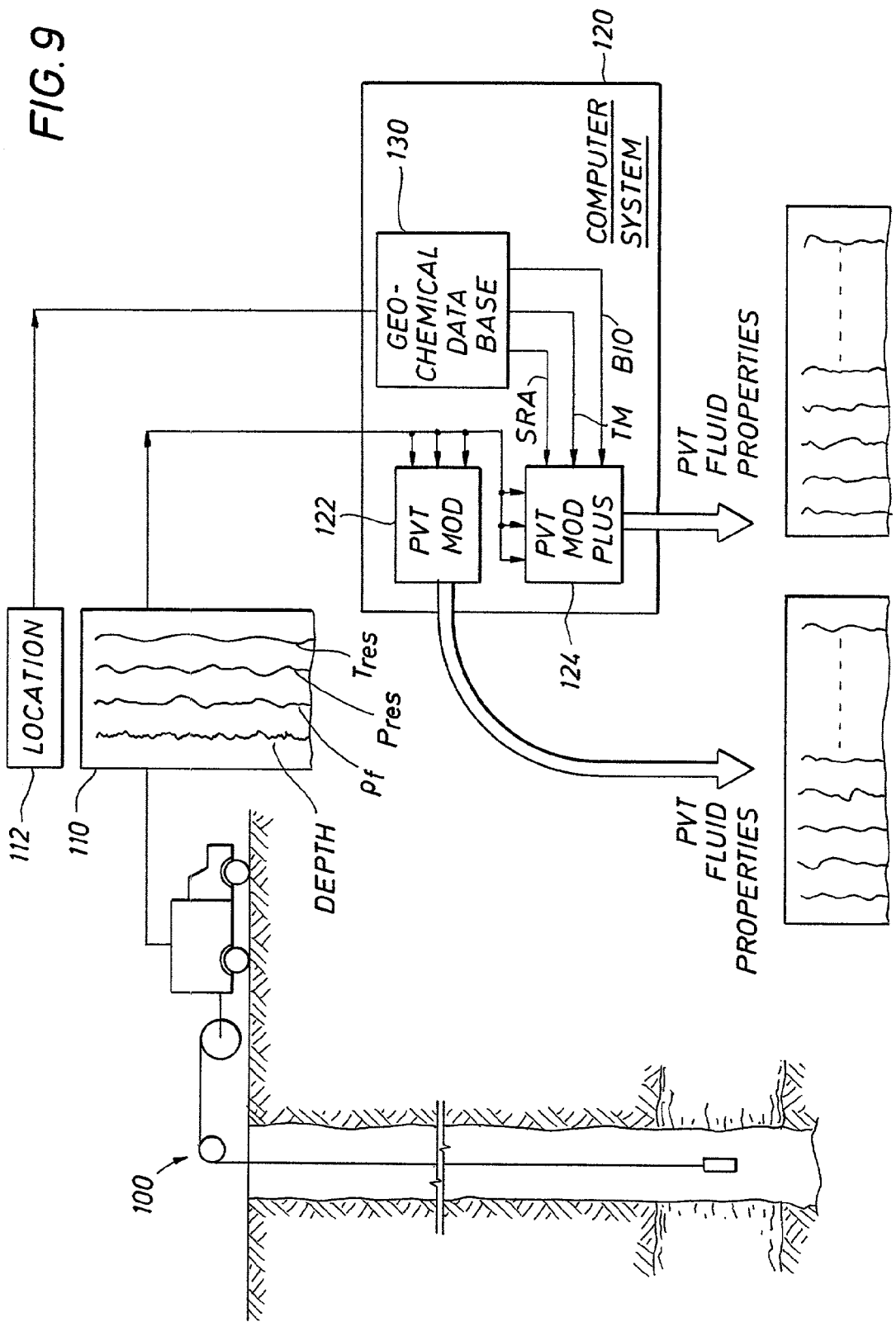
FIG. 9 is a schematic illustration of a system for producing PVT fluid properties solely from wireline logging information or from wireline logging information plus geochemical information from the location of the well under investigation.

FIG. 9 is a schematic illustration of a Wireline Formation Test tool such as a downhole formation testing system offered commercially by Schlumberger Well Services and other companies. Such logging system generates a log 110 for a well, the location of which is known, as symbolized by the information (Logic Box 112). The log includes data as a function of depth such as $P_{res}$ and $T_{res}$ and $\rho_f$ after calculation of density from the change in $P_{res}$ as a function of depth. A computer system 120 is provided which includes at least one (or both) of the equation modules described above called PVT MOD 122 or PVT MOD PLUS 124. The computer system also includes a stored database 130 which relates a location of any well in the world to at least one of three fundamental geochemical characteristics of oil, such as source rock aromaticity (SRA), Thermal Maturity (TM) and Biodegradation (BIO).

PVT Fluid Properties as a function of depth are produced without geochemical parameters by applying log information to the PVT MOD module 122. PVT Fluid Properties as a function of depth are also produced as a function of depth by applying the log information to the PVT MOD PLUS module 124 and also applying at least one geochemical characteristics from the group, SRA, TM, BIO by first applying location information to geochemical database 130.

In summary, the invention is for a method and system for predicting PVT fluid properties and phase behavior parameters based on standard downhole measurements from a Wireline Formation Test tool. Such measurements are formation pressure, formation temperature and pressure gradient. The output PVT fluid properties and phase behavior parameters, all related to the input measurements, by a set of equations called PVT MOD, as described above include one or more of the following:

Saturation Pressure (Bubble and Dew Point)
Gas Oil Ratio (GOR) from Single-Stage Flash
Saturated Formation Volume Factor (FVF) from Single-Stage Flash
Reservoir Fluid Density
Reservoir Fluid Viscosity
Reservoir Fluid Molecular Weight
Reservoir Fluid Composition ($C_1$ to $C_{7+}$, $N_2$, $CO_2$)
Reservoir Fluid Heavy Ends Characterization ($C_{7+}$ Molecular Weight and Specific Gravity)
API Gravity of Stock Tank Oil from Single-Stage Flash
Sulfur Content of Stock Tank Oil from Single-Stage Flash
Flash Gas Gravity from Single-Stage Flash
Flash Gas Gross Heating Value The method further includes a method for predicting PVT fluid properties and phase behavior parameters based on the standard downhole measurements as above, but also based on input data about the geochemical properties of the expected petroleum fluid. Such geochemical input data includes source rock aromaticity, thermal maturity and biodegradation.

The method described above was used in an interpretative study to develop PVT MOD PLUS equations based on stock tank oil geochemistry and reservoir fluid PVT data from 145 samples in the Gulf of Mexico as described above. Source rock aromaticity, thermal maturity and biodegradation indicators were developed from 45 Regional Studies and contained in a database called GeoMark GLOBAL OILS™ database of 3,700 samples available commercially from GeoMark Research, Inc. of Houston, Tex. In other words, given the location of a well, the database yields data specific to that location as to the three geochemical parameters mentioned above.

The PVT parameters and well location information was applied to the PVT MOD PLUS module 124 and geochemical database 130 to produce PVT fluid properties parameters as indicated in FIG. 9. The predicted or "calculated" parameters based on well log measurements were compared with actual surface based laboratory results for a given depth, for many samples collected by WFT tools. Similar tests of the method and apparatus for predicting PVT fluid properties were completed against a PVT/geochemical data set from oil reservoirs offshore eastern Canada. The results compared favorably to the test of Gulf of Mexico data.

APPENDIX I

I. Equations Corresponding to Table 1
   a. Reservoir Fluid Viscosity, μ

$$\mu_{\rho_f < 0.75 g/cc} = k_1 + k_2 \exp\left(\frac{\rho_f}{k_3}\right) \qquad (6)$$

$$\mu_{\rho_f < 0.75 g/cc} = \left(k_4 + \frac{k_5}{\ln(k_6)}\right)^2 \qquad (7)$$

b. Reservoir Fluid Methane Content, $C_1$ $$C_{1\ RFMW<50\ g/mole} = k_7 + k_8 \rho_f^{0.5} \ln(\rho_f) + k_9 P_{res}^2 \ln(P_{res}) + k_{10} T_{res}^{1.5} \quad (8)$$

$$C_{1\ RFMW \geq 50\ g/mole} = k_{11} + k_{12} \rho_f^{0.5} \ln(\rho_f) + k_{13} P_{res}^2 \ln(P_{res}) + k_{14} T_{res}^{1.5} \quad (9)$$

c. Reservoir Fluid Heptane+Content, $C_{7+}$ $$C_{7+} = \exp\left(k_{15} + \frac{k_{16}}{\rho_f^{0.5}}\right) \quad (10)$$

d. Reservoir Fluid Molecular Weight, RFMW $$RFMW = \exp(k_{17} + k_{18} P_{res} + (k_{19} + k_{20} P_{res}) \rho_f^{1.5} + k_{21} T_{res}^2) \quad (11)$$

e. Gas Oil Ratio, GOR $$GOR_{RFMW<60\ g/mole} = \exp\left(k_{22} + \frac{k_{22}}{\ln(RFMW)} + \frac{k_{23}}{RFMW)^{0.5}}\right) \quad (12)$$

$$GOR_{RFMW<60\ g/mole} = k_{24} + \frac{k_{25}}{(RFMW)^2} \quad (13)$$

f. Stock Tank Oil Sulfur Content, % S $$\%S = \exp\left(k_{26} + \frac{k_{27} \ln(RFMW)}{(RFMW)^2}\right) \quad (14)$$

g. Saturated Formation Volume Factor, FVF $$FVF_{RFMW>50\ g/mole} = (k_{28} + k_{29} \exp(\rho_f))^{-1} \quad (15)$$

h. Reservoir Fluid Nitrogen Content, $N_2$ $$N_2 = k_{30} + k_{31}(RFMW)\ln(RFMW) \quad (16)$$

i. Reservoir Fluid Carbon Dioxide Content, $CO_2$ $$CO_2 = k_{32} + k_{33} \rho_f \quad (17)$$

j. Reservoir Fluid Heptane+Molecular Weight, $C_{7+}MW$ $$C_{7+}MW = k_{34} + k_{35} \ln(\%S) \quad (18)$$

k. Reservoir Fluid Heptane+Specific Gravity, $C_{7+}SG$ $$C_{7+}SG = k_{36} + k_{37}(\%S)^{0.5} \quad (19)$$

l. Saturation Pressure, $P_{sat}$ $$P_{sat\ \rho_f > 0.82\ g/cc} = k_{38} + k_{39}(\ln(\rho_f))^2 + k_{40} \ln(T_{res}) \quad (20)$$

$$P_{sat\ \rho_f > 0.53\ g/cc} = k_{41} + k_{42}(\ln(\rho_f))^2 + k_{43} \ln(T_{res}) \quad (21)$$

$$P_{sat\ C_1 > 90\ mole\%} = k_{44} + \frac{k_{45}}{C_1^2} + \frac{k_{46} \ln(C_{7+}MW)}{(C_{7+}MW)^2} \quad (22)$$

$$P_{sat\ C_1 > 90\ mole\%} = k_{47} + \frac{k_{48}}{C_1^2} + \frac{k_{49}}{\ln\left(\frac{C_1}{\rho_f}\right)} \quad (23)$$

m. Stock Tank Oil PI Gravity, API $$API = \left(k_{50} + \frac{k_{51}}{\ln(C_{7+}SG)}\right)^{-1} \quad (24)$$

n. Reservoir Fluid Ethane Content, $C_2$ $$C_2 = \left(\frac{(C_1 + k_{52}(C_{7+}) + k_{53})}{k_{54}}\right)^2 \quad (25)$$

o. Reservoir Fluid Propane Content, $C_3$ $$C_3 = \left(\frac{(C_1 + k_{55}(C_{7+}) + k_{56})}{k_{57}}\right)^2 \quad (26)$$

p. Reservoir Fluid i-Butane Content, $iC_4$ $$iC_4 = k_{58} + k_{59}(nC_4)^{0.5} \quad (27)$$

q. Reservoir Fluid n-Butane Content, $nC_4$ $$nC_4 = \left(\frac{(C_1 + k_{60}(C_{7+}) + k_{61})}{k_{62}}\right)^2 \quad (28)$$

r. Reservoir Fluid i-Pentane Content, $iC_5$ $$iC_5 = \exp(k_{63} + k_{64} \ln(nC_5)) \quad (29)$$

s. Reservoir Fluid n-Pentane Content, $nC_5$ $$nC_5 = \left(\frac{(C_1 + k_{65}(C_{7+}) + k_{66})}{k_{67}}\right)^2 \quad (30)$$

t. Reservoir Fluid Hexanes Content, $C_6$ $$C_6 = \left(\frac{(C_1 + k_{68}(C_{7+}) + k_{69})}{k_{70}}\right)^2 \quad (31)$$

u. Flash Gas Gravity, FGG $$FGG = \exp\left(k_{71} + \frac{k_{72}(Wetness)}{\ln(Wetness)}\right) \quad (32)$$

$$\text{where: } Wetness = \frac{100(C_2 + C_3 + iC_4 + nC_4)}{(C_1 + C_2 + C_3 + iC_4 + nC_4)} \quad (33)$$

v. Flash Gas Gross Heating Value, FGGHV $$FGGHV = k_{73} + k_{74}(FGG)^2 \ln(FGG) + \frac{k_{75}}{FGG} \quad (34)$$

II. Equations Corresponding to Table 2 a. Reservoir Fluid Viscosity, $\mu$ $$\mu_{\rho_f < 0.75\ g/cc} = k_{76} + k_{77} \exp\left(\frac{\rho_f}{k_{78}}\right) \quad (35)$$

$$\mu_{\rho_f \geq 0.75\ g/cc} = \left(k_{79} + \frac{k_{80}}{\ln(k_{81})}\right)^2 \quad (36)$$

b. Reservoir Fluid Methane Content, $C_1$ $$C_{1\ RFMW<50\ g/mole} = k_{82} + k_{83}\rho_f^{0.5}\ln(\rho_f) + k_{84}P_{res}^2\ln(P_{res}) + k_{85}T_{res}^{1.5} \quad (37)$$

$$C_{1\ RFMW\geq 50\ g/mole} = k_{86} + k_{87}\rho_f^{0.5}\ln(\rho_f) + k_{88}P_{res}^2\ln(P_{res}) + k_{89}T_{res}^{1.5} + k_{90}\frac{\ln(SRA)}{(SRA)^2} + k_{91}TM^{k_{92}} + k_{93}(Bio.) \quad (38)$$

c. Reservoir Fluid Heptane+Content, $C_{7+}$ $$C_{7+} = \exp\left(k_{94} + \frac{k_{95}}{\rho_f^{0.5}} + k_{96}(SRA)^{0.5}\ln(SRA) + k_{97}\frac{TM}{\ln(TM)}\right) \quad (39)$$

d. Reservoir Fluid Molecular Weight, RFMW $$RFMW = \exp\left(\begin{array}{c}k_{98} + k_{99}P_{res} + (k_{100} + k_{101}P_{res})\rho_f^{1.5} + k_{102}T_{res}^2 + \\ k_{103}(SRA)^{k_{104}} + k_{105}(TM)^{k_{106}}\end{array}\right) \quad (38)$$

e. Gas Oil Ratio, GOR $$GOR_{RFMW<60\ g/mole} = \exp\left(k_{107} + \frac{k_{108}}{\ln(RFMW)} + \frac{k_{109}}{(RFMW)^{0.5}}\right) \quad (39)$$

$$GOR_{RFMW\geq 60\ g/mole} = k_{110} + \frac{k_{111}}{(RFMW)^2} + k_{112}(Bio.) \quad (40)$$

f. Stock Tank Oil Sulfur Content, % S $$\%S = \exp\left(k_{113} + \frac{k_{114}\ln(RFMW)}{(RFMW)^2} + \frac{k_{115}(SRA)^2}{\ln(SRA)} + k_{116}(Bio.)\right) \quad (41)$$

g. Saturated Formation Volume Factor, FVF $$FVF_{RFMW>50\ g/mole} = (k_{117} + k_{118}\exp(\rho_f) + k_{119}(SRA)^3)^{-1} \quad (42)$$

h. Reservoir Fluid Nitrogen Content, $N_2$ $$N_2 = k_{120} + k_{121}(RFMW)\ln(RFMW) + k_{122}\ln(SRA) \quad (43)$$

i. Reservoir Fluid Carbon Dioxide Content, $CO_2$ $$CO_2 = k_{123} + k_{124}\rho_f + \frac{k_{125}\ln(SRA)}{(SRA)^2} + \frac{k_{126}}{(SRA)^2} \quad (44)$$

j. Reservoir Fluid Heptane+Molecular Weight, $C_{7+}MW$ $$C_{7+}MW = k_{127} + k_{128}\ln(\%S) + k_{129}(SRA)^{0.5} \quad (45)$$

k. Reservoir Fluid Heptane+Specific Gravity, $C_{7+}SG$ $$C_{7+}SG = k_{130}\ k_{131}(\%S)^{0.5} + k_{132}(SRA)^3 \quad (46)$$

l. Saturation Pressure, $P_{sat}$ $$P_{sat\ \rho_f>0.82\ g/cc} = k_{133} + k_{134}(\ln(\rho_f))^2 + k_{135}\ln(T_{res}) \quad (47)$$

$$P_{sat\ \rho_f>0.53\ g/cc} = k_{136} + k_{137}(\ln(\rho_f))^2 + k_{138}\ln(T_{res}) + k_{139}(TM)^3 \quad (48)$$

-continued $$P_{sat\ C_1>90\ mole\ \%} = k_{140} + \frac{k_{141}}{C_1^2} + \frac{k_{142}\ln(C_{7+}MW)}{(C_{7+}MW)^2} \quad (49)$$

$$P_{sat\ C_1\leq 90\ mole\ \%} = k_{143} + \frac{k_{144}}{C_1^2} + \frac{k_{145}}{\ln\left(\frac{C_1}{\rho_f}\right)} \quad (50)$$

m. Stock Tank Oil PI Gravity, API $$API = \left(k_{146} + \frac{k_{147}}{\ln(C_{7+}SG)} + k_{148}(SRA)\ln(SRA)\right)^{-1} \quad (51)$$

n. Reservoir Fluid Ethane Content, $C_2$ $$C_2 = \left(\frac{(C_1 + k_{149}(C_{7+}) + k_{150})}{k_{151}}\right)^2 \quad (52)$$

o. Reservoir Fluid Propane Content, $C_3$ $$C_3 = \left(\frac{(C_1 + k_{152}(C_{7+}) + k_{153})}{k_{154}}\right)^2 \quad (53)$$

p. Reservoir Fluid i-Butane Content, $iC_4$ $$iC_4 = k_{155} + k_{156}(nC_4)^{0.5} + k_{157}(SRA)^{0.5}\ln(SRA) \quad (54)$$

q. Reservoir Fluid n-Butane Content, $nC_4$ $$nC_4 = \left(\frac{(C_1 + k_{158}(C_{7+}) + k_{159})}{k_{160}}\right)^2 \quad (55)$$

r. Reservoir Fluid i-Pentane Content, $iC_5$ $$iC_5 = \exp(k_{161} + k_{162}\ln(nC_5) + k_{163}(SRA)^{0.5}\ln(SRA)) \quad (56)$$

s. Reservoir Fluid n-Pentane Content, $nC_5$ $$nC_5 = \left(\frac{(C_1 + k_{164}(C_{7+}) + k_{165})}{k_{166}}\right)^2 \quad (57)$$

t. Reservoir Fluid Hexanes Content, $C_6$ $$C_6 = \left(\frac{(C_1 + k_{167}(C_{7+}) + k_{168})}{k_{169}}\right)^2 \quad (58)$$

u. Flash Gas Gravity, FGG $$FGG = \exp\left(k_{170} + \frac{k_{171}(Wetness)}{\ln(Wetness)} + k_{172}(SRA)\ln(SRA)\right) \quad (59)$$

$$\text{where: Wetness} = \frac{100(C_2 + C_3 + iC_4 + nC_4)}{(C_1 + C_2 + C_3 + iC_4 + nC_4)} \quad (60)$$

v. Flash Gas Gross Heating Value, FGGHV $$FGGHV = k_{173} + k_{174}(FGG)^2 \ln(FGG) + \frac{k_{175}}{FGG} \qquad (61)$$

| OUTPUT PVT VARIABLE | INPUT VARIABLE(S) |
|---|---|
| Reservoir Fluid Viscosity ($\mu$) | $\rho_f$ |
| Reservoir Fluid Methane Content ($C_1$) | $\rho_f$, $P_{res}$, $T_{res}$, SRA, TM, BIO |
| Reservoir Fluid Heptane+ Content ($C_{7+}$) | $\rho_f$, SRA, TM |
| Reservoir Fluid Molecular MW (RFMW) | $\rho_f$, SRA, TM, $P_{res}$, $T_{res}$ |
| Single-Stage Gas Oil Ratio (GOR) | RFMW, BIO |
| Stock Tank Oil Sulfur Content (% S) | RFMW, SRA, BIO |
| Saturated Formation Volume Factor (FVF) | RFMW, $T_{res}$ |
| Reservoir Fluid Nitrogen Content ($N_2$) | RFMW, SRA |
| Reservoir Fluid Heptane+ Mw ($C_{7+}$MW) | % S, SRA |
| Reservoir Fluid Heptane+ SG ($C_{7+}$SG) | % S, SRA |
| Saturation Pressure ($P_{sat}$) | $C_1$, SRA, TM, $C_{7+}$MW, $T_{res}$ |
| Stock Tank Oil API Gravity (API) | $C_{7+}$SG, SRA |
| Reservoir Fluid Ethane Content ($C_2$) | $C_1$, $C_{7+}$ |
| Reservoir Fluid Propane Content ($C_3$) | $C_1$, $C_{7+}$ |
| Reservoir Fluid i-Butane Content ($iC_4$) | $nC_4$, SRA |
| Reservoir Fluid n-Butane Content ($nC_4$) | $C_1$, $C_{7+}$ |
| Reservoir Fluid i-Pentane Content ($iC_5$) | $nC_5$, SRA |
| Reservoir Fluid n-Pentane Content ($nC_5$) | $C_1$, $C_{7+}$ |
| Reservoir Fluid Hexane Content ($C_6$) | $C_1$, $C_{7+}$ |
| Flash Gas Gravity (Gas Gravity) | $C_1$, $C_2$, $C_3$, $iC_4$, $nC_4$, SRA |
| Flash Gas Gross Heating Value (BTU/scf) | Gas Gravity |

What is claimed is:

1. A method of predicting a pressure-volume-temperature (PVT) fluid property of a selected reservoir comprising:
   a. generating a regression model from a set of prior data that comprises a plurality of measurements of the PVT fluid property such that the regression model relates the PVT fluid property as a function of reservoir pressure and reservoir temperature;
   b. measuring reservoir pressure and reservoir temperature at a location in a wellbore that penetrates at least a portion of the selected reservoir; and
   c. predicting the PVT fluid property of the selected reservoir utilizing the measured reservoir pressure and reservoir temperature and the generated regression model.

2. The method of claim 1 wherein the reservoir pressure is used to calculate a reservoir fluid density.

3. The method of claim 1 wherein the set of prior data further comprise a measurement corresponding to a geochemical parameter.

4. The method of claim 1 wherein predicting the PVT fluid property of the selected reservoir is done without recovery of a fluid sample.

5. The method of claim 1 wherein the reservoir pressure is used to calculate a pressure gradient.

6. The method of claim 3 wherein the geochemical parameter is related to a geographical location of the selected reservoir and the geographical location is used by the regression model to predict the PVT fluid property.

7. A method for predicting a pressure-volume-temperature (PVT) fluid property of a selected reservoir, comprising:
   a. generating a regression model from a set of prior data that comprises a plurality of measurements of the PVT fluid property such that the regression model relates the PVT fluid property as a function of reservoir pressure, reservoir temperature, reservoir fluid density, and a geochemical parameter wherein the geochemical parameter is related to a geographic location of the selected reservoir;
   b. storing the regression model in a computer system;
   c. measuring well log data at a location in a wellbore, the well log data comprising reservoir pressure, reservoir temperature and reservoir fluid density;
   d. estimating the geochemical parameter using the geographic location of the selected reservoir; and
   e. inputting reservoir pressure, reservoir temperature, reservoir fluid density and the geographical location of the selected reservoir to the regression model stored in the computer system to predict the PVT fluid property.

8. The method of claim 7, wherein the geochemical parameter comprises at least one of: (i) a source rock aromaticity; (ii) a thermal maturity; and (iii) a bio-degradation.

9. The method of claim 7 wherein predicting the PVT fluid property of the selected reservoir is done without recovery of a fluid sample.

10. An apparatus for predicting a pressure-volume-temperature (PVT) fluid property of a selected reservoir, comprising:
    a. a formation test tool deployed in a wellbore penetrating at least a portion of the selected reservoir, the formation test tool adapted to measure a reservoir pressure and a reservoir temperature at a location in the wellbore; and
    b. a computer system having a regression model therein, the computer system in communication with the formation test tool, the regression model relating the PVT fluid property as a function of the reservoir pressure and the reservoir temperature.

11. The apparatus of claim 10, wherein the regression model further relates the PVT fluid property to a geochemical parameter.

12. The apparatus of claim 11, wherein the geochemical parameter comprises at least one of: (i) a source rock aromaticity; (ii) a thermal maturity; and (iii) a bio-degradation.

* * * * *